United States Patent [19]
Kennedy

[11] Patent Number: 5,993,376
[45] Date of Patent: Nov. 30, 1999

[54] ELECTROMAGNETIC INPUT TRANSDUCERS FOR MIDDLE EAR SENSING

[75] Inventor: Joel A. Kennedy, Arden Hills, Minn.

[73] Assignee: St. Croix Medical, Inc., Minneapolis, Minn.

[21] Appl. No.: 08/907,424

[22] Filed: Aug. 7, 1997

[51] Int. Cl.⁶ ............................................. H04R 25/00
[52] U.S. Cl. ........................... 600/25; 607/55; 181/129
[58] Field of Search ............................. 600/25; 607/55, 607/56, 57; 181/129, 130, 131, 132, 133, 134, 135

[56] References Cited

U.S. PATENT DOCUMENTS

| 3,870,832 | 3/1975 | Frederickson | 600/25 |
|---|---|---|---|
| 4,547,631 | 10/1985 | Nieuwendijk et al. | 179/115.5 R |
| 4,606,329 | 8/1986 | Hough | 600/25 |
| 4,628,907 | 12/1986 | Epley | 128/1.6 |
| 4,696,287 | 9/1987 | Hortmann et al. | 128/1 R |
| 4,729,366 | 3/1988 | Schaefer | 607/57 |
| 4,756,312 | 7/1988 | Epley | 128/420.5 |
| 4,774,933 | 10/1988 | Hough et al. | 600/25 |
| 4,776,322 | 10/1988 | Hough et al. | 128/1.6 |
| 4,800,884 | 1/1989 | Heide et al. | 128/419 R |
| 4,817,607 | 4/1989 | Tatge | 600/25 |
| 4,840,178 | 6/1989 | Heide et al. | 128/419 R |
| 4,850,962 | 7/1989 | Schaefer | 600/25 |
| 4,936,305 | 6/1990 | Ashtiani et al. | 128/420.6 |
| 4,957,478 | 9/1990 | Maniglia | 600/25 |
| 5,012,236 | 4/1991 | Troyk et al. | 340/825.54 |
| 5,012,520 | 4/1991 | Steeger | 381/68 |
| 5,015,224 | 5/1991 | Maniglia | 600/25 |
| 5,015,225 | 5/1991 | Hough et al. | 600/25 |
| 5,015,255 | 5/1991 | Hough et al. | 600/25 |
| 5,163,957 | 11/1992 | Sadé et al. | 623/10 |
| 5,220,918 | 6/1993 | Heide et al. | 128/420.6 |
| 5,259,032 | 11/1993 | Perkins et al. | 381/68 |
| 5,277,694 | 1/1994 | Leysieffer et al. | 600/25 |
| 5,311,449 | 5/1994 | Adams | 364/514 |
| 5,338,287 | 8/1994 | Miller et al. | 600/25 |
| 5,360,388 | 11/1994 | Spindel et al. | 600/25 |
| 5,383,915 | 1/1995 | Adams | 607/60 |
| 5,456,654 | 10/1995 | Ball | 600/25 |
| 5,554,096 | 9/1996 | Ball | 600/25 |
| 5,558,618 | 9/1996 | Maniglia | 600/25 |
| 5,624,376 | 4/1997 | Ball et al. | 607/55 |
| 5,730,699 | 3/1998 | Adams et al. | 600/25 |

FOREIGN PATENT DOCUMENTS

| 39 18 329 A1 | 12/1990 | Germany . |
|---|---|---|
| 196 18 961 A1 | 11/1997 | Germany . |
| 196 38 158 A1 | 4/1998 | Germany . |
| 196 38 159 A1 | 4/1998 | Germany . |

OTHER PUBLICATIONS

Fredrickson, M.D., J.M., et al., "Ongoing Investigations into an Implantable Electromagnetic Hearing Aid for Moderate to Severe Sensorineural Hearing Loss," Otolaryngologic Clinics of North America, 28:107–120, (1995).

Glorig, A., et al., "Magnetically Coupled Stimulation of the Ossicular Chain: Measures in Kangaroo Rat and Man," Journal of the Acoustical Society of America, 52:694–696, (1972).

(List continued on next page.)

Primary Examiner—Max Hindenburg
Assistant Examiner—Charles Marmor, II
Attorney, Agent, or Firm—Patterson & Keough, P.A.

[57] ABSTRACT

A hearing assistance system senses sound vibrations of an auditory element in the middle ear and provides a stimulus to an auditory sensory element. The vibrations are received through the tympanic membrane, and sensed at the tympanic membrane, malleus, incus, or other auditory element. An electromagnetic sensor includes receiving and reference elements, e.g. a permanent magnet and a coil, having a time-varying magnetic flux linkage due to the vibrations. The magnet and coil are pivotably coupled to an auditory element and a carrier, or vice-versa, for self-alignment. A resulting electrical signal on the coil is processed, then provided to an output stimulator for mechanical or electrical stimulation of the cochlea.

10 Claims, 5 Drawing Sheets

OTHER PUBLICATIONS

Goode, M.D., R.L., "Current Status of Electromagnetic Implantable Hearing Aids," Otolaryngologic Clinics of North America, 28:201–209, (1989).

Goode, M.D., R.L., "Electromagnetic Implantable Hearing Aids," Advances in Audiology (Kargar, Basel), 4:22–31, (1988).

Goode, M.D., R.L., et al., "Audition Via Electromagnetic Induction," Archives of Otolaryngology, 98:23–26, (1973).

Gulya, M.D., J., et al., Hearing Aids: II. Implantable Hearing Aids, Archives of Otolaryngology Head and Neck Surgery, 122:363–367, (1996).

Hough, M.D., J.V.D., et al., "Long–Term Results for the Xomed Audiant Bone Conductor," Otolaryngologic Clinics of North America, 28:43–53, (1995).

Hough, M.D., J., et al., "Middle Ear Implantable Hearing Device: Ongoing Animal and Human Evaluation," Ann. Otol. Rhinol. Laryngol, 97:650–658, (1988).

Kartush, M.D., J.M., "Electromagnetic Ossicular Augmentation Device," Otolaryngologic Clinics of North America, 28:155–172, (1995).

Maniglia, M.D., A.J., et al., "Contactless Semi–Implantable Electromagnetic Middle Ear Device for the Treatment of Sensorineural Hearing Loss: Short–Term and Long–Term Animal Experiments," Otolaryngologic Clinics of North America, 28:121–140, (1995).

Maniglia, M.D., A.J., et al., "Electromagnetic Implantable Middle Ear Hearing Device of the Ossicular–Stimulating Type: Principles, Designs, and Experiments," Ann. Otol. Rhinol Laryngol, 97 (Suppl 136), part 2, (1988).

Suzuki, J., et al., "Middle Ear Implant for Humans," Acta Otolaryngol, 99:313–317, (1985).

Wilpizeski, PhD., C., et al., "A Simple Implantable Electromechanical Middle Ear," Transactions of the Pennsylvania Academy of Ophthalmology and Otolaryngology, 32:41–46, (1979).

Yanagihara, N., et al., "Implantable Hearing Aid," Archives of Otolaryngology Head and Neck Surgery, 113: 869–872, (1987).

Maniglia, M.D., A.J., "A Contactless Electromagnetic Implantable Middle Ear Device for Sensorineural Hearing Loss," Ear, Nose and Throat Journal, 73(2), (1994).

Ko, PhD., W.H., "A Preliminary Study on the Implantable Middle Ear Hearing Aid," I.E.E.E. 9th Annual Conference on Engineering in Medicine and Biology Society, (1987).

Gyo, M.D., K., et al., "Present Status and Outlook of the Implantable Hearing Aid," American Journal of Otology, 11:250–253, (1990).

Goode, M.D., R.L., "Current Status and Future of Implantable Electromagnetic Hearing Aids," Otolaryngologic Clinics of North America, 28:141–146, (1995).

Buchman, E., et al., "On the Transmission of Sound Generated by an Electromagnetic Device from the Mastoid Process to the Petrous Bone," Journal of the Acoustical Society of America, 90:895–903, (1991).

Goode, R.L., "Implantable Hearing Devices," Medical Clinics of North America, 75:1261–1266, (1991).

Hough, M.D., J., "A Middle Ear Implantable Hearing Device for Controlled Amplification of Sound in the Human: A Preliminary Report," Laryngoscope, 97:141–151, (1987).

Kartush, M.D., J.M., et al., "Electromagnetic Semi–Implantable Hearing Device: An Update," Otolaryngology Head and Neck Surgery, 104:150 (1990).

McGee, M.D., T.M., et al., "Electromagnetic Semi–Implantable Hearing Device; Phase I. Clinical Trials," Laryngoscope, 101:355, (1991).

Maniglia, A.J., et al., "Design, Development, and Analysis of a Newer Electromagnetic Semi–Implantable Middle Ear Hearing Device," Transplants and Implants in Otology II, 365–369, (1991).

ELECTROMAGNETIC INPUT TRANSDUCERS FOR MIDDLE EAR SENSING

CROSS REFERENCE TO RELATED APPLICATIONS

This application is related to co-pending, commonly assigned U.S. patent application "MIDDLE EAR VIBRATION SENSOR USING MULTIPLE TRANSDUCERS," Ser. No. 08/908,236, filed on even date herewith and assigned to the assignee of the present application, which disclosure is herein incorporated by reference.

THE FIELD OF THE INVENTION

This invention relates generally to at least partially implantable hearing assistance systems, and more particularly to the sensing of sound vibrations in the middle ear.

BACKGROUND

Some types of partial middle ear implantable (P-MEI), total middle ear implantable (T-MEI), cochlear implant, or other hearing assistance systems utilize components disposed within the middle ear or inner ear regions. Such components may include an input transducer for receiving sound vibrations or an output stimulator for providing mechanical or electrical output stimuli corresponding to the received sound vibrations.

An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus bone in the patient's middle ear. The malleus vibrates in response to sounds received at the patient's tympanic membrane (eardrum). The piezoelectric input transducer transduces mechanical energy of malleus vibrations into an electrical signal, which is amplified and further processed by an electronics unit. A resulting electrical signal is provided to an electrical-to-mechanical piezoelectric output transducer that generates a mechanical vibration coupled to an element of the ossicular chain or to the oval window or round window. In the '366 patent, the ossicular chain is interrupted by removal of the incus. Removal of the incus prevents the mechanical vibrations delivered by the piezoelectric output transducer from mechanically feeding back to the piezoelectric input transducer.

Another example of such a device is disclosed in U.S. Pat. No. 5,554,096 issued to G. R. Ball on Sep. 10, 1996. In the '096 patent, an external transducer senses sound. A resulting electrical signal is processed and provided to a subcutaneous electromagnetic transducer. In the '096 patent, the electromagnetic transducer is used for vibrating an ossicle.

Another example of such a device is disclosed in U.S. Pat. No. 5,558,618 issued to A. J. Maniglia on Sep. 24, 1996. In the '618 patent, acoustic signals are transduced into electrical signals by external means. A resulting electrical signal is provided to actuate an electromagnet for assisting hearing.

Hearing assistance systems that use piezoelectric input transducers to sense sounds through corresponding ossicular vibrations face numerous difficulties. For example, the bandwidth of the piezoelectric input transducer may not accommodate the full frequency band between 250 Hertz and 5 kilohertz needed for good speech comprehension. Piezoelectric input transducers also typically suffer from a highly nonlinear frequency response due to a resonance frequency in or near the audio frequency range. Piezoelectric input transducers can be quite fragile. In addition, a piezoelectric input transducer typically requires rigid mechanical contact with the auditory element, which results in a mechanical loading that can diminish the gain and frequency sensitivity of the sensed mechanical sound vibrations.

For the reasons stated above, and for other reasons stated below which will become apparent to those skilled in the art upon reading and understanding the present specification, there is a need in the art for sensing middle ear sound vibrations through input transducers that do not have the above-described limitations of piezoelectric input transducers.

SUMMARY

The present invention provides a hearing assistance system that includes non-piezoelectric input sensors for transducing vibrations in the middle ear into electrical signals. One embodiment of the invention includes an electromechanical sensor including an electromagnetic element. Another embodiment includes a middle-ear implantable hearing assistance system having an electromagnetic sensor, coupled to an auditory element for receiving vibrations and providing a resulting electrical input signal. An electronics unit is electrically coupled to the electromagnetic sensor for processing the input signal. An output stimulator receives from the electronics unit a signal based on the input signal. The output stimulator provides a resulting stimulus to an auditory element. In one embodiment, the hearing assistance system includes an external programmer for adjusting hearing assistance parameters in a hearing assistance device and for data transmission from the hearing assistance device to the programmer, such as for parameter verification or diagnostic purposes.

The invention also provides a method of transducing mechanical vibrations of an auditory element into at least one electrical signal. A receiving element is coupled to an auditory element for receiving the vibrations. A reference element is disposed for electromagnetic communication with the receiving element. A time-varying electromagnetic coupling is sensed between the receiving and reference elements resulting from the vibrations.

According to one aspect of the invention, at least one of the first and second portions of the transducer is adapted for pivotable coupling to the auditory element and a carrier, respectively. In one embodiment, the first portion of the transducer is a magnet pivotably coupled to the auditory element, and the second portion of the transducer includes a coil that is pivotably coupled to the auditory element. The magnet extends coaxially at least partially within the coil. As a result, self-alignment is obtained between the magnet and coil.

Thus, the present invention provides alternatives to piezoelectric input transducers, which have limited and nonlinear frequency characteristics, potential reliability problems associated with their durability, and mechanical loading that can diminish the gain and frequency sensitivity of the sensed mechanical sound vibrations.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views.

The teachings of the present invention disclose a hearing assistance system for sensing mechanical vibrations of an auditory element that avoids the above-described limitations of piezoelectric input transducers. The invention is capable of use as or with a middle ear implantable hearing system such as a partial middle ear implantable (P-MEI), total middle ear implantable (T-MEI), cochlear implant, or other hearing system. A P-MEI or T-MEI hearing system assists the human auditory system in converting acoustic energy contained within sound waves into electrochemical signals delivered to the brain and interpreted as sound.

Figure 1:
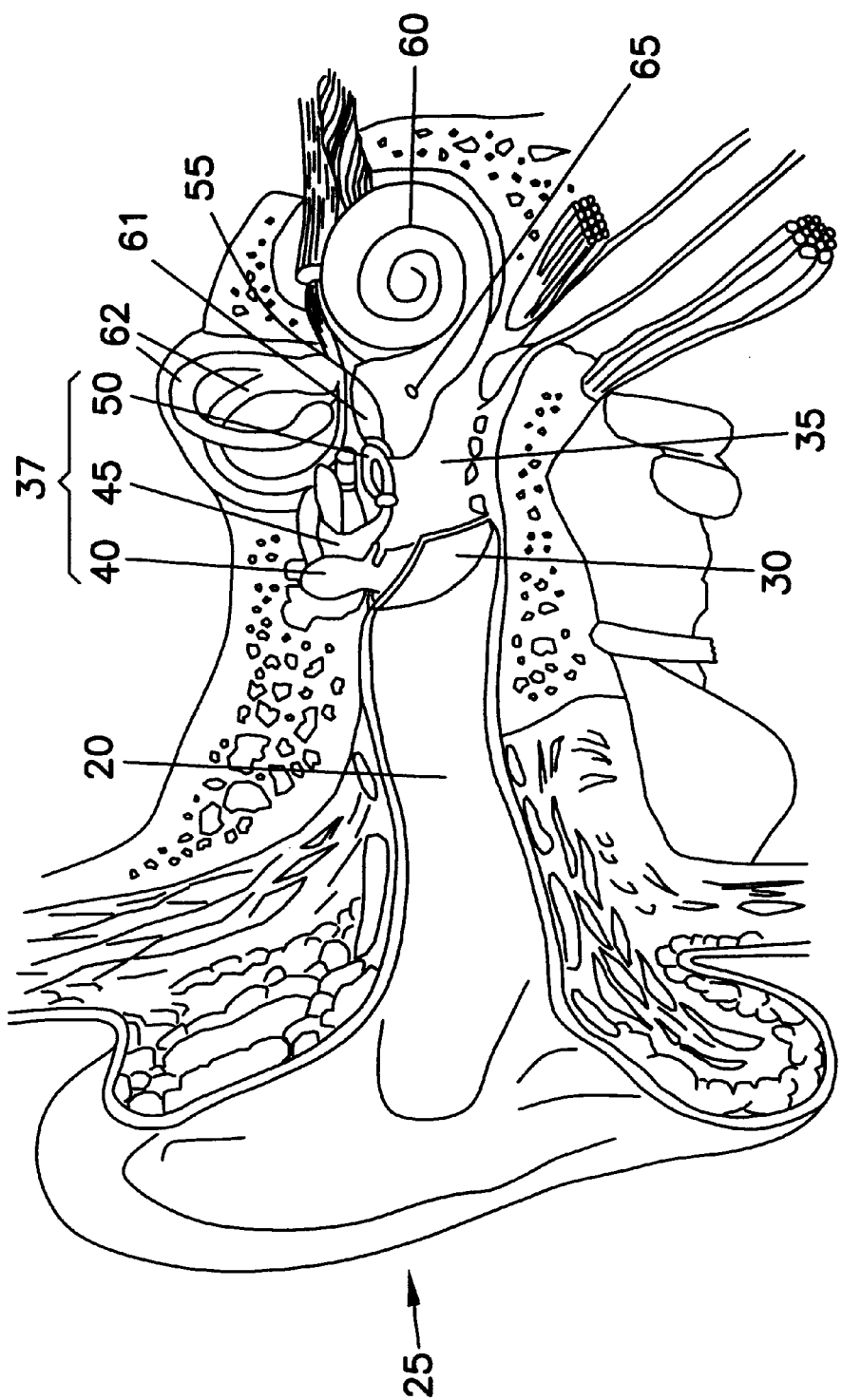
FIG. 1 illustrates generally a human auditory system.

FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three ossicles: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea 60 is referred to as sensorineural hearing loss. Hearing loss due to an inability to conduct mechanical vibrations through the middle ear 35 is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing systems have also been developed, utilizing various approaches to compensate for hearing disorders. For example, cochlear implant techniques implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing systems have been developed to aid patients without an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow coupling of the mechanical vibrations thereto. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer. As described above, piezoelectric input transducers have certain limitations, including with respect to frequency response, durability, and mechanical loading of the sensed auditory element. As described below, the teachings of the present invention disclose a hearing assistance system for sensing mechanical vibrations of an auditory element that avoids such limitations.

Figure 2:
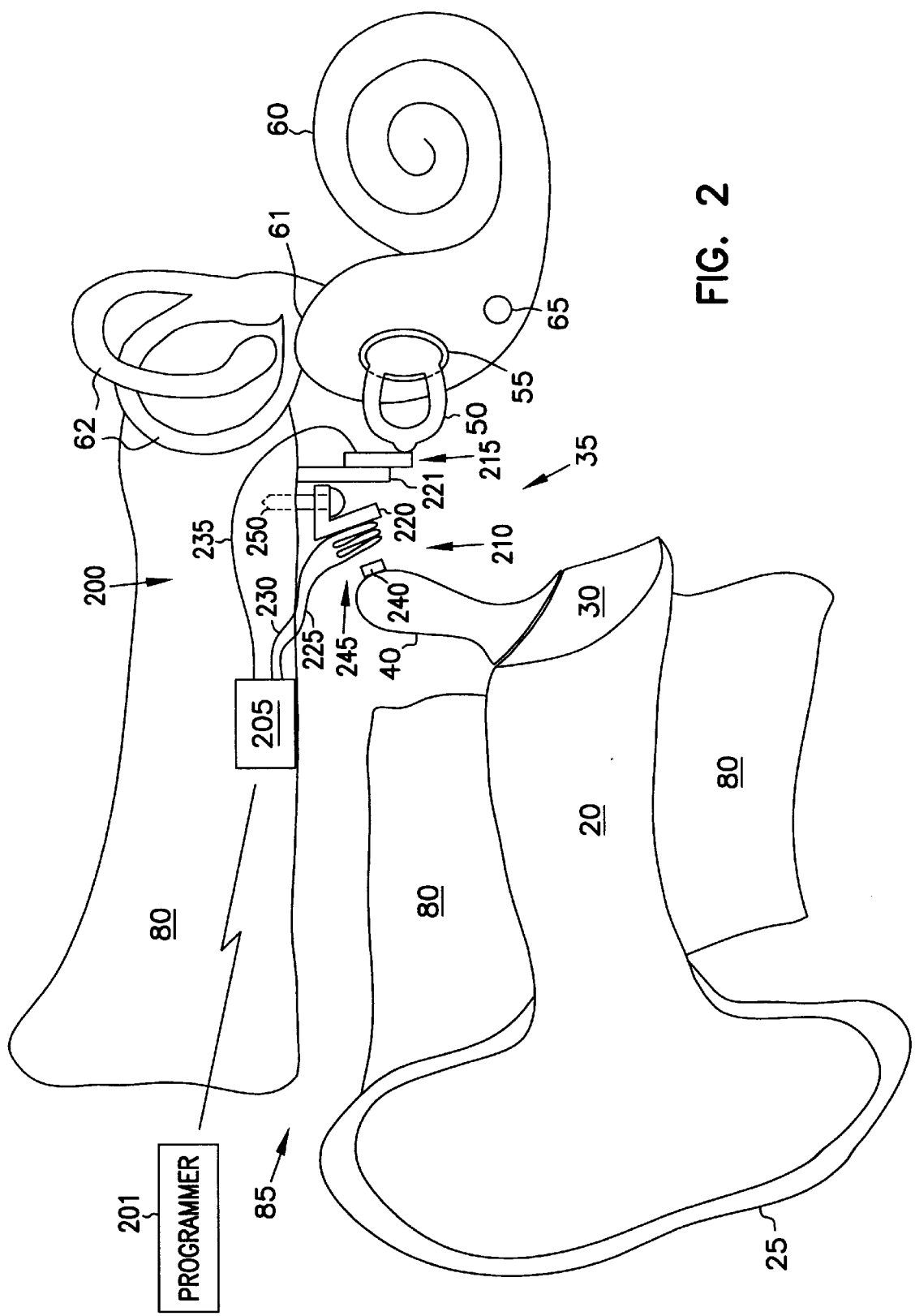
FIG. 2 is a schematic/block diagram illustrating generally one embodiment of a hearing assistance system according to the present invention, including an electromagnetic input sensor.

FIG. 2 is a schematic/block diagram illustrating generally one embodiment of a hearing assistance system according to one embodiment of the present invention. This embodiment includes hearing assistance device 200, of which at least a portion is implanted in the middle ear 35 and optionally in the mastoid 80 portion of the temporal bone. In this embodiment, incus 45 is removed. However, such removal of incus 45 is not required to practice the invention. Hearing assistance device 200 includes electronics unit 205, an input sensor 210, and an output stimulator 215. A carrier 220 is provided, such as for mounting portions of input sensor 210 and output stimulator 215.

The hearing assistance system also includes an external (i.e., not implanted) programmer 201, which is communicatively coupled to an external or implantable portion of hearing assistance device 200. Programmer 201 includes hand-held, desktop, or a combination of hand-held and desktop embodiments, for use by a physician or the patient in which hearing assistance device 200 is implanted.

In one embodiment, each of programmer 201 and hearing assistance device 200 include an inductive element, such as a coil, for inductively-coupled bi-directional transdermal communication between programmer 201 and hearing assistance device 200. Inductive coupling is just one way to communicatively couple programmer 201 and hearing assistance device 200. Any other suitable technique of communicatively coupling programmer 201 and hearing assistance device 200 may also be used.

In one embodiment, such communication includes programming of hearing assistance device 200 by programmer 201 for adjusting hearing assistance parameters in hearing assistance device 200, and also provides data transmission from hearing assistance device 200 to programmer 201, such as for parameter verification or diagnostic purposes. Programmable parameters include, but are not limited to: on/off, standby mode, type of noise filtering for a particular sound environment, frequency response, volume, delivery of a test stimulus on command, and any other programmable parameter.

Input sensor 210 senses the mechanical sound vibrations of an auditory element, and provides a resulting electrical input signal in response thereto. In the embodiment of FIG. 2, malleus 40 is illustrated, by way of example, as the auditory element from which vibrations are sensed, but other auditory elements could also be used, including, but not limited to tympanic membrane 30, incus 45 or other ossicle, or any prosthetic auditory element serving a similar function. Input sensor 210 provides the resulting electrical input signal, such as through lead wires at nodes 225 and 230, to electronics unit 205. Electronics unit 205 receives the input signal that is based on a changing magnetic flux linkage resulting from the sensed vibrations of the auditory element. Electronics unit 205 provides amplification, filtering, or other signal processing of the input signal, and provides a resulting electrical output signal, such as through one or more lead wires, illustrated generally by node 235, to output stimulator 215. Output stimulator 215 is secured by carrier 221 within middle ear 35 and provides mechanical or electrical stimulation of the inner ear. In the embodiment of FIG. 2, for example, output stimulator 215 transmits mechanical vibrations to oval window 55 of cochlea 60 through stapes 50.

In the embodiment of FIG. 2, input sensor 210 includes a receiving element 240 and a reference element 245. Receiving element 240 is mechanically coupled to the auditory element, such as by affixation to malleus 40, for receiving vibrations of the auditory element that result from sound. The vibratory motion of the auditory element is also imparted to the receiving element 240. In this embodiment, the position of reference element 245 is substantially fixed with respect to the vibrating receiving element 240. In FIG. 2, for example, reference element 245 is affixed to carrier 220, which is secured to mastoid 80 by bone screw 250. In another embodiment, reference element 245 could also be directly affixed to mastoid 80, or otherwise secured by any suitable technique. In this embodiment, receiving element 240 and reference element 245 are in contactless communication with each other, such as described below.

In this embodiment, receiving element 240 and reference element 245 are electromagnetically coupled. For example, receiving element 240 includes a permanent magnet providing a magnetic field, and reference element 245 includes a coil which links a portion of the magnetic flux arising from the magnetic field provided by the magnet. The vibrations of receiving element 240, cause variations in the magnetic flux linked by the coil reference element 245, producing a resulting voltage across the terminals of reference element 245. This electrical voltage input signal is provided to electronics unit 205 through lead wires, such as at nodes 225 and 230. One skilled in the art will appreciate that many voltage amplification techniques that are known in the art will provide suitable voltage amplification and buffering reference element 245.

Figure 3:
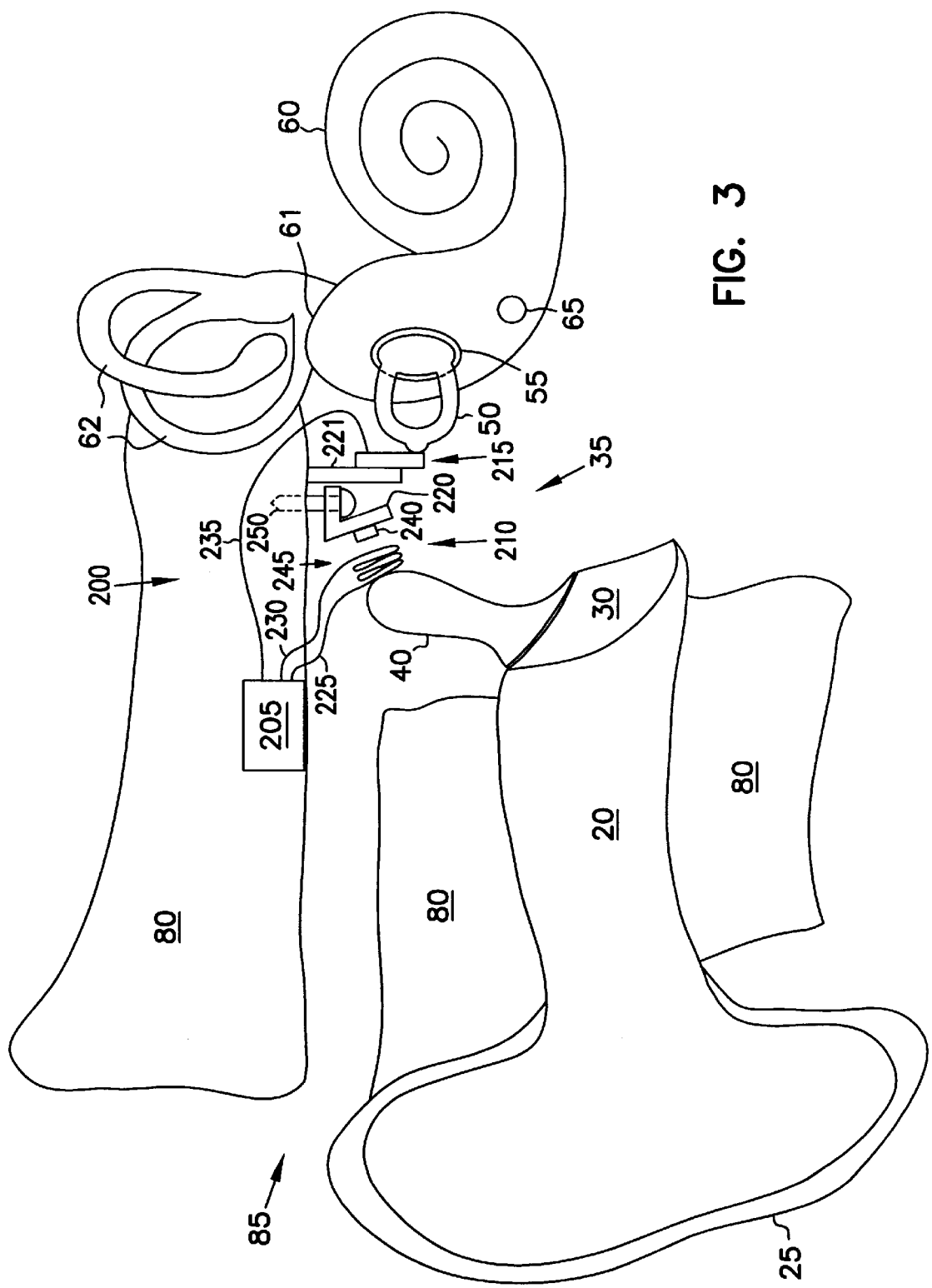
FIG. 3 is a schematic/block diagram illustrating generally an alternative embodiment of the input sensor of FIG. 2.

FIG. 3 is a schematic/block diagram illustrating generally an alternate embodiment of the invention, in which receiving element 240 includes a coil, and reference element 245 includes a permanent magnet. In this embodiment, the coil receiving element 240 undergoes vibratory motion with respect to a fixed-position permanent magnet reference element 245, causing a time-varying magnetic flux linked by coil receiving element 240. A resulting electrical input signal is provided by coil receiving element 240 to electronics unit 205 through lead wires, such as at nodes 225 and 230.

Figure 4:
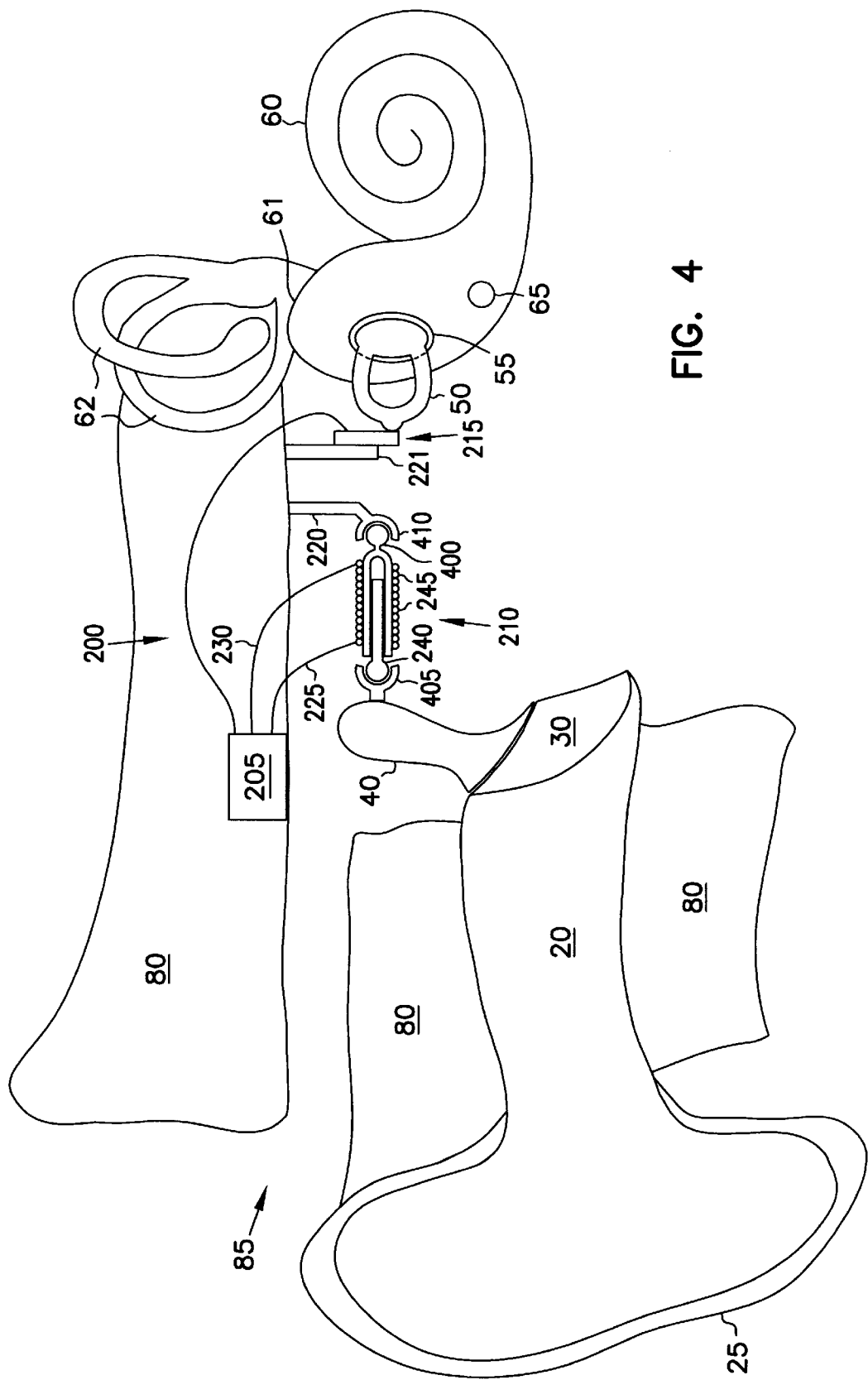
FIG. 4 is a schematic block diagram illustrating generally another alternative embodiment of the input sensor of FIG. 2.

FIG. 4 is a schematic/block diagram, similar to FIG. 2, illustrating generally another embodiment in which the permanent magnet of receiving element 240 is a bar magnet that extends coaxially at least partially within the region circumferentially enclosed by a sleeve 400 carrying coil reference element 245. In this embodiment, the coaxial receiving element 240 undergoes vibratory motion with respect to the fixed-position sleeve 400 and coil reference element 245, causing a time-varying magnetic flux linked by reference element 245. A resulting electrical input signal is provided by coil reference element 245 to electronics unit 205 through lead wires, such as at nodes 225 and 230.

In one embodiment, for example, receiving element 240 is pivotably secured to the auditory element (e.g., malleus 40), such as by a socket 405 that receives a ball portion at one end of receiving element 240, the other end of receiving element 240 at least partially received by sleeve 400. In a further embodiment, for example, sleeve 400 is pivotably secured to carrier 220, such as by a socket 410 portion of carrier 220 that receives a ball portion at one end of sleeve 400, the other end of sleeve 400 engaging receiving element 240. The pivotable coupling of at least one of the receiving element 240 and sleeve 400 to malleus 40 and carrier 220, respectively, advantageously allows self-alignment of receiving element 240 with respect to sleeve 400 and reference element 245. The pivotable coupling of each of the receiving element 240 and sleeve 400 to malleus 40 and carrier 220, respectively, advantageously allows further flexibility in the self-alignment of receiving element 240 with respect to sleeve 400 and reference element 245.

In an alternative embodiment, receiving element 240 includes a sleeve, carrying a coil and affixed to the vibrating auditory element, and reference element 245 includes a bar magnet at least partially received by the sleeve such that the vibrating sleeve and coil both move with respect to the bar magnet.

Figure 5:
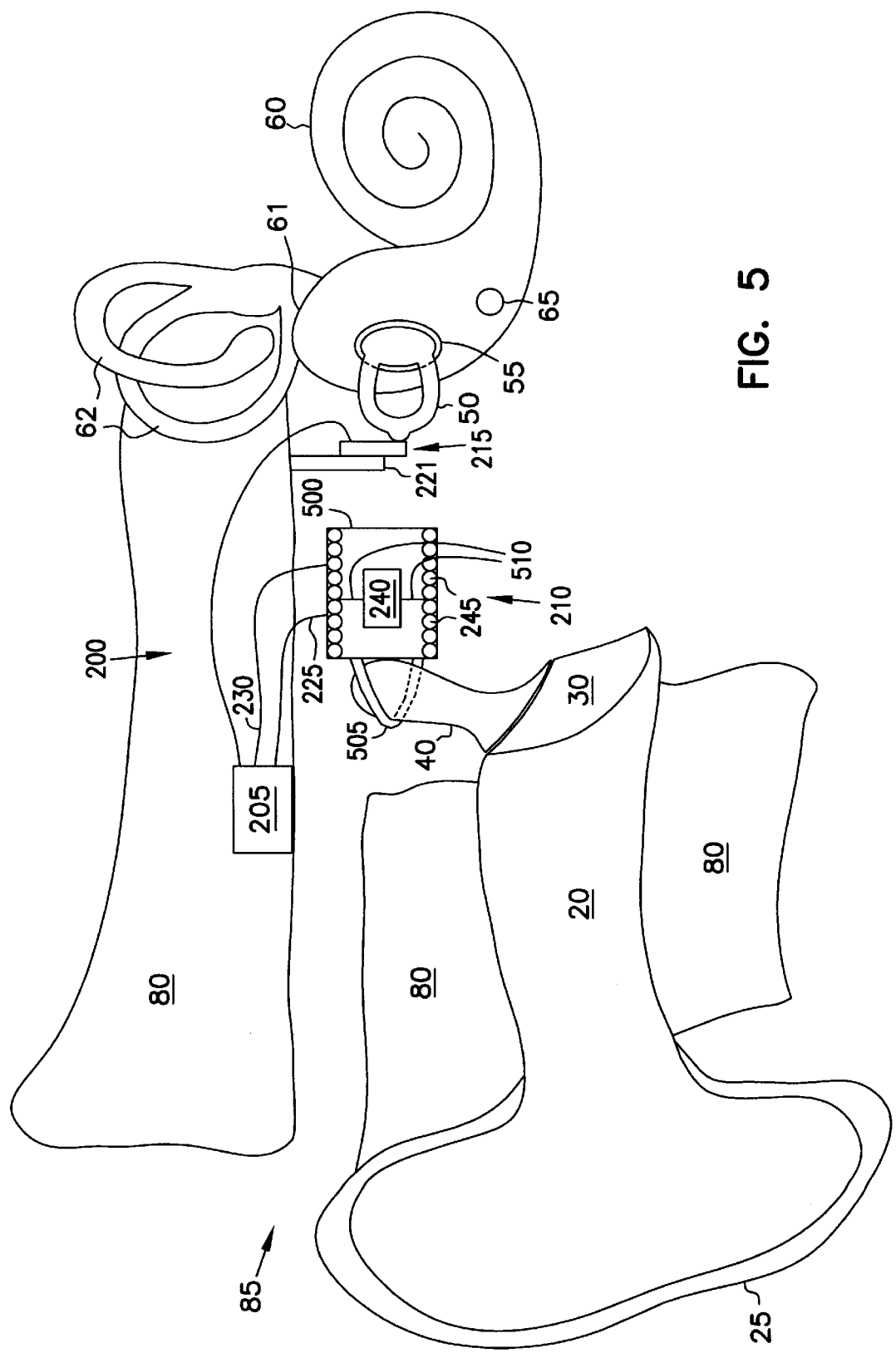
FIG. 5 is a schematic/block diagram illustrating generally another alternative embodiment of the input sensor of FIG. 2.

FIG. 5 is a schematic/block diagram illustrating generally an alternate embodiment of the invention, in which both receiving element 240 and reference element 245 are mechanically coupled to the vibrating auditory element, e.g. malleus 40, such as through carrier 500. Receiving element 240 is mechanically coupled to reference element 245, as described below. In this embodiment, carrier 500 is secured to malleus 40 by a crimped wire 505, or any other suitable means of mechanical, adhesive, or other affixation. Receiving element 240 is a permanent magnet that is elastically coupled to carrier 500, e.g. by one or more elastic mounts 510, and which functions as an accelerometer mass. Receiving element 240 is circumferentially enclosed by coil reference element 245. The vibrations of the auditory element are mechanically coupled to the permanent magnet receiving element 240, causing it to vibrate with respect to the reference element 245. As a result, a time-varying magnetic flux is linked by the reference element 245. A resulting electrical input signal is provided by the coil reference element 245 to electronics unit 205 through lead wires, such as at nodes 225 and 230.

CONCLUSION

The present invention includes an improved hearing assistance system for sensing sound vibrations of an auditory element in the middle ear and providing a stimulus to an auditory sensory element in response thereto. The present invention provides alternatives to piezoelectric input transducers, which have limited and nonlinear frequency characteristics, potential reliability problems associated with their durability, and mechanical loading that can diminish the gain and frequency sensitivity of the sensed mechanical sound vibrations. Moreover, one aspect of the invention allows sound to pass through the tympanic membrane, incorporating its natural frequency reception characteristics into the sensed vibrations.

It is to be understood that the above description is intended to be illustrative, and not restrictive. Combinations of the above-described embodiments are within the scope of the present invention. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An electromechanical transducer proportioned for disposition in a middle ear, the transducer comprising:
   a first portion proportioned for mechanical coupling to an auditory element;
   a second portion proportioned for disposition in the middle ear; and a carrier, carrying the second portion of the transducer, and adapted to be secured in the middle ear, wherein at least one of the first and second portions of the transducer is adapted for pivotable coupling to the auditory element and carrier, respectively, and wherein at least one of the portions adapted for pivotable coupling includes a ball and socket.

2. The transducer of claim 1, wherein the first portion includes a magnet and the second portion includes a coil that is electromagnetically coupled to the magnet.

3. The transducer of claim 2, wherein the magnet extends coaxially at least partially within the coil.

4. The transducer of claim 1, wherein the first portion includes a coil and the second portion includes a magnet that is electromagnetically coupled to the coil.

5. The transducer of claim 4, wherein the magnet extends coaxially at least partially within the coil.

6. An at least partially implantable hearing assistance system, comprising:

an electromagnetic sensor, pivotably coupled with a ball and socket to an auditory element for receiving vibrations and providing a resulting electrical input signal;

an electronics unit, electrically coupled to the electromagnetic sensor for processing the input signal; and an output stimulator, receiving from the electronics unit a signal based on the input signal, and providing a resulting stimulus to an auditory element.

7. The system of claim 6, further comprising a programmer adapted to be communicatively coupled to the electronics unit.

8. The system of claim 7, wherein the programmer and electronics unit are adapted to be inductively coupled.

9. A method of transducing mechanical vibrations of an auditory element into at least one electrical signal, the method comprising the steps of:

pivotably coupling a receiving element to an auditory element for receiving the vibrations;

disposing a reference element for electromagnetic communication with the receiving element; and sensing a time-varying electromagnetic coupling between the receiving and reference elements resulting from the vibrations, wherein said pivotably coupled receiving element comprises a ball and socket joint.

10. The method of claim 9, further comprising the step of receiving the vibrations through a tympanic membrane.

\* \* \* \* \*